United States Patent
Duburs et al.

(10) Patent No.: US 8,492,413 B2
(45) Date of Patent: Jul. 23, 2013

(54) PHARMACEUTICAL COMBINATION OF 5-FLUOROURACIL AND DERIVATE OF 1,4-DIHYDROPYRIDINE AND ITS USE IN THE TREATMENT OF CANCER

(75) Inventors: Gunars Duburs, Riga (LV); Egils Bisenieks, Riga (LV); Irina Sestakova, Riga (LV); Ivars Kalvinsh, Ikskile (LV); Brigita Vigante, Riga (LV); Janis Uldrikis, Jelgava (LV); Ilona Domraceva, Riga (LV); Elina Jascenko, Riga (LV); Janis Poikans, Riga (LV); Imanta Bruvere, Riga (LV); Ilmars Stonans, Riga (LV)

(73) Assignee: JSC Grindeks, Riga (LV)

( * ) Notice: Subject to any disclaimer, the term of this patent is extended or adjusted under 35 U.S.C. 154(b) by 52 days.

(21) Appl. No.: 13/138,614

(22) PCT Filed: Mar. 11, 2010

(86) PCT No.: PCT/EP2010/053094
§ 371 (c)(1),
(2), (4) Date: Sep. 9, 2011

(87) PCT Pub. No.: WO2010/103067
PCT Pub. Date: Sep. 16, 2010

(65) Prior Publication Data
US 2012/0022088 A1 Jan. 26, 2012

(30) Foreign Application Priority Data

Mar. 11, 2009 (EP) .................................. 09154872
Apr. 30, 2009 (EP) .................................. 09159197
Oct. 22, 2009 (EP) .................................. 09173816

(51) Int. Cl.
*A61K 31/44* (2006.01)
*C07D 213/80* (2006.01)

(52) U.S. Cl.
USPC .................................... 514/356; 546/321

(58) Field of Classification Search
None
See application file for complete search history.

(56) References Cited

U.S. PATENT DOCUMENTS
4,293,700 A 10/1981 Uldrikis et al.

OTHER PUBLICATIONS

International Serach Report for PCT/EP2010/053094 of May 3, 2010.
Uldrikis, J., et al., Akademiya Nauk Latviiskoi S.S.R. Izvestiya, No. 1, p. 122-123, Jan. 1, 1983.
Zidermane, A., et al., Experimental Oncology, vol. 9, No. 2, p. 50-52, Jan. 1, 1987.

*Primary Examiner* — Zinna Northington Davis
(74) *Attorney, Agent, or Firm* — Hueschen and Sage

(57) ABSTRACT

New compounds of 2,6-dimethyl-1,4-dihydropyridine-3,5-dicarboxylic acid ester type having general formula I

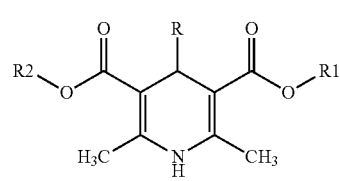

wherein R is a lower alkyl group, which is methyl or ethyl $R_1$ and $R_2$ is sodium carboxylate-methyl ester, having synergistic cytotoxic effect combined with 5-fluorouracil.

11 Claims, No Drawings

PHARMACEUTICAL COMBINATION OF 5-FLUOROURACIL AND DERIVATE OF 1,4-DIHYDROPYRIDINE AND ITS USE IN THE TREATMENT OF CANCER

CONTINUING DATA

This application is a 371 of PCT/EP2010/053094 filed Mar. 11, 2010.

TECHNICAL FIELD

The present invention relates to new water-soluble 2,6-dimethyl-1,4-dihydropyridine-3,5-dicarboxylic acid ester type compounds having general formula I

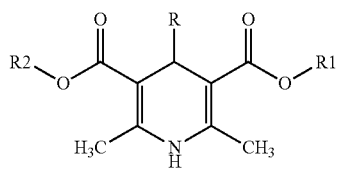

wherein R is a lower alkyl group, which is methyl or ethyl
$R_1$ and $R_2$ is sodium carboxylate-methyl ester
New water-soluble 2,6-dimethyl-1,4-dihydropyridine-3,5-dicarboxylic acid ester type compounds with general formula I have a synergistic cytotoxic effect in combination with 5-fluorouracil.

BACKGROUND ART

Cancer is a leading cause of death in animals and humans. Several efforts have been and are still being undertaken in order to obtain active and safe antitumour agents to be administered to patients suffering from a cancer. The problem to be solved by the present invention is to provide further compounds that are useful in the treatment of cancer.

5-Fluorouracil (5-FU) is a fluorinated pyrimidine analogue that has been widely used as an antimetabolic anticancer agent for the treatment and palliative management of various forms of cancer including colorectal, pancreatic, breast, and stomach cancer. It is frequently prescribed to subjects whose cancers are considered incurable. Despite its demonstrated clinical usefulness, there are a number of serious disadvantages associated with the use of 5-fluorouracil which can be dose-limiting and which may render patients unable to tolerate treatment using 5-fluorouracil.

There is a significant need in the art for novel compounds, compositions, and methods that are useful for treating cancer with improved therapeutic indications by potenting anticancer effect of 5-fluorouracil.

Disodium salt of carboxylate-methyl ester of 2,6-dimethyl-1,4-dihydropyridine-3,5-dicarboxylic acid (Carbatone) with antimetastatic activity, which is disclosed in WO 80/00345 A (INST ORGANICHESKOGO SINTEZA) 06.03.1980, is the most similar compound to 2,6-dimethyl-1,4-dihydropyridine-3,5-dicarboxylic acid ester type compounds having general formula I.

The same Carbatone was described in ZIDERMANE, A, et al. Potentiating effect of disodium salt of 2,6-dimethyl-1,4-dihydropyridine-3,5-bis-carbonyl hydroxyacetic acid on the activity of various antitumor agents. *Eksp Onkol.* 1987, vol. 9, no. 2, p. 50-2. wherein it was used for decreasing the cyclophosphane toxicity in mice and potentiates the cytostatic activity of cyclophosphane, 5-fluorouracil and arabisosyl cytosine against leukaemia P388, murine sarcoma 37 and Walker's carcinosarcome. As it was described that Carbatone exhibited no antitumour activity.

In ULDRIKIS, J., et al. 1,4-Dihydropyridine derivatives as a means for potentiating the action of antitumor preparations. *LATVIJAS PSR ZINATNU AKADEMIJAS VESTIS, KIMIJAS SERIJA.* 1983, vol. 1, p. 122-123. is described that disodium salt of carboxylate-methyl ester of 2,6-dimethyl-1,4-dihydropyridine-3,5-dicarboxylic acid (Carbatone) increase antitumour activity of 5-fluorouracil.

DISCLOSURE OF INVENTION

An object of the present invention is to provide compounds, which would effectively and synergistically potentiates the cytotoxic effect of 5-FU.

The above-mentioned object is attained by providing new water-soluble compounds of 2,6-dimethyl-1,4-dihydropyridine-3,5-dicarboxylic acid ester type having general formula I

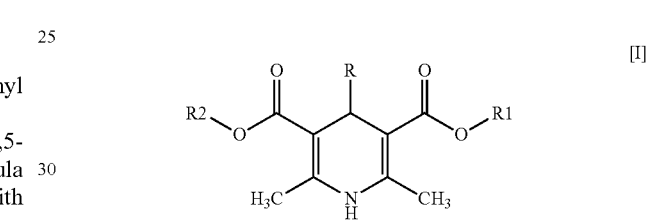

wherein R is lower alkyl group, such as methyl or ethyl
$R_1$ and $R_2$ is sodium carboxylate-methyl ester
The compounds according of formula I are:
disodium salt of 2,4,6-trimethyl-1,4-dihydropyridine-3,5-bis-carbonyloxyacetic acid, having formula IV

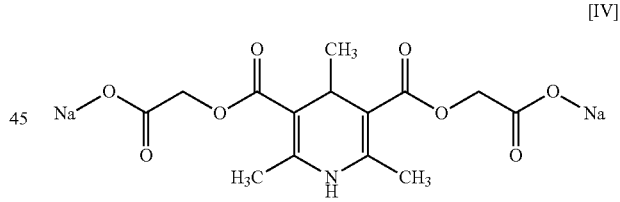

disodium salt of 4-ethyl-2,6-dimethyl-1,4-dihydropyridine-3,5-bis-carbonyloxyacetic acid, having formula VI

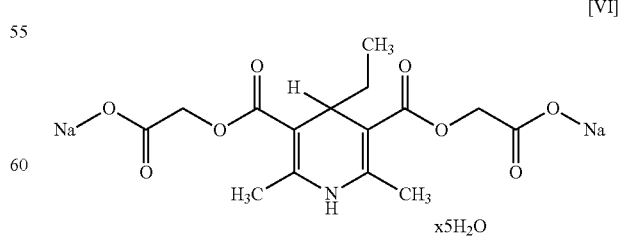

The compounds having general formula I synergistically potentiates the cytotoxic effect of 5-FU, due this properties compounds having general formula I, may be used in medicine. The compounds having general formula I can be use as a solution of injection and as tablets.

An object of the present invention is a method of preparation of said compounds of formula I.

The common process for the preparation of 2,6-dimethyl-1,4-dihydropyridine-3,5-dicarboxylic acid ester type compounds comprises condensation of two molecules of derivative of acetoacetic acid ester, formaldehyde and ammonia. Thereafter treat with sodium hydroxide in ethanol.

BEST MODE FOR CARRYING OUT THE INVENTION

Example 1

Preparation of Disodium Salt of 2,4,6-trimethyl-1,4-dihydropyridine-3,5-bis-carbonyloxyacetic acid

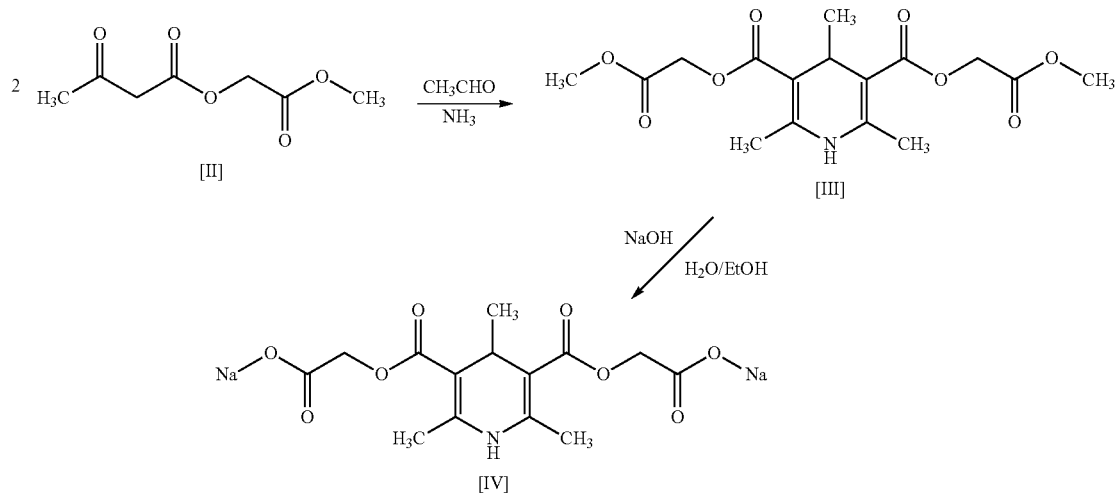

2-Methoxycarbonyl methyl ester of acetoacetate (2 mol) was condensed with acetoaldehyde (1 mol) and ammonia (1 mol). Thereafter 2,4,6-trimethyl-3,5-bis(methoxycarbonyl-methoxycarbonyl)-1,4-dihydropyridine is treated with sodium hydroxide in ethanol.

Disodium salt of 2,4,6-trimethyl-1,4-dihydropyridine-3,5-bis-carbonyloxyacetic acid was dried at ambient temperature. Yield 76%. Having melting point of 278-280° C.

$^1$H-NMR spectrum (400 MHz, CDCl$_3$) δ: 0.90 (3H, d, J=6.5 Hz, 4-CH$_3$); 2.19 (6H, s, 2,6-CH$_3$); 3.76 (1H, kv, J=6.5 Hz, 4-H); 4.15 and 4.23 (4H, AB quartet, J=16 Hz, 3,5-COOCH$_2$CO); 8.56 (1H, pl.s, NH)

Example 2

Preparation of Disodium Salt of 4-ethyl-2,6-dimethyl-1,4-dihydropyridine-3,5-bis-carbonyloxyacetic acid

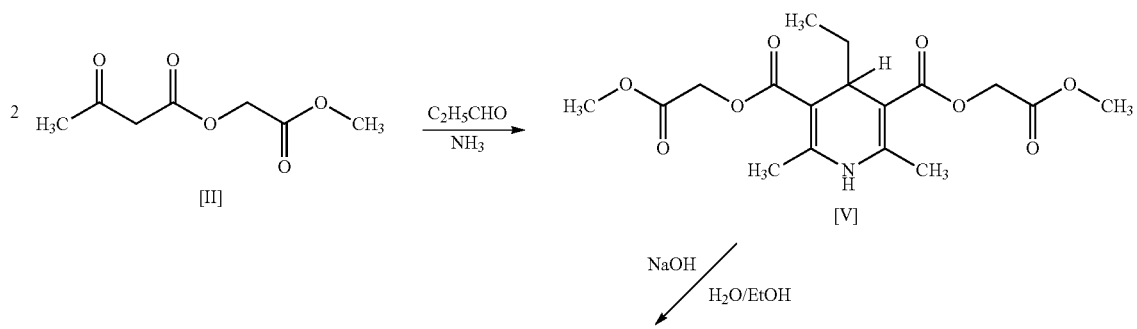

-continued

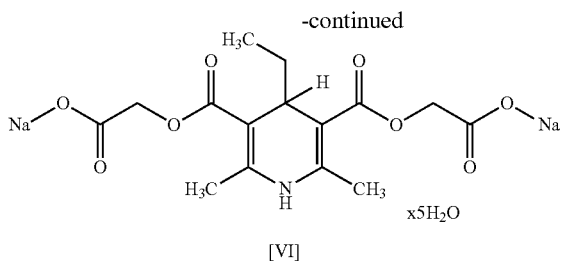

[VI]

2-Methoxycarbonyl methyl ester of acetoacetate (2 mol) was condensed with propionaldehyde (1 mol) and ammonia (1 mol). Thereafter 4-ethyl-2,6-dimethyl-1,4-dihydropyridine-3,5-bis-carbonyloxyacetic acid is treated with sodium hydroxide in ethanol.

Disodium salt of 4-ethyl-2,6-dimethyl-1,4-dihydropyridine-3,5-bis-carbonyloxyacetic acid was dried at ambient temperature.

Having melting point of 65-67° C.

$^1$H-NMR spectrum (400 MHz, DMSO, TMS) δ: 0.59 (3H, tr, CH$_3$); 1.23-1.24 (2H, m, CH$_2$CH$_3$); 2.17 (6H, s, 2.6-CH$_3$); 3.80 (1H, tr, 4-CH); 4.10 (4H, kv, —CH2-); 8.30 (1H, s, N—H).

Example 3

A new 2,6-dimethyl-1,4-dihydropyridine-3,5-dicarboxylic acid ester type compounds with general formula I, were evaluated for anticancer efficacy by examining their cytotoxic effects on human breast cancer cells MDA-MB-435s in vitro alone and in combination with 5-fluorouracil.

Cell Culture and Measurement of Cell Viability

MDA-MB-435s cells were seeded in 96-well plates in Dulbecco's modified Eagle's medium containing 10% fetal bovine serum, w/o antibiotics an cultivated for 72 h by exposure to different concentrations of 5-fluorouracil and 2,6-dimethyl-1,4-dihydropyridine-3,5-dicarboxylic acid ester type compounds. Cell viability was measured using modified crystal violet staining (CVS) assay as described in [Segarman et al., 1985]. In brief, cells were fixed with 1% glutaraldehyde for 15 minutes, washed with water and stained with 0.05% crystal violet for 15 minutes at room temperature. After removal of residual crystal violet by washing with tap water the crystal violet stain was eluted with ethanol sodium citrate (1:1) buffer, and absorbance at 540 nm was measured using a microplate reader.

The IC$_{50}$ values, corresponding to concentrations of compounds that cause 50% cell viability decrease, were calculated for individual compounds and their combinations and are summarized in Table 1.

Results of IC$_{50}$ combined treatment with 2,6-dimethyl-1,4-dihydropyridine-3,5-dicarboxylic acid ester type compounds, having general formula I, and 5-FU are summarized in Table 1.

TABLE 1

| Combination of compounds | | IC$_{50}$ | |
|---|---|---|---|
| Compound 1 | Compound 2 | Compound 1 [μM] | Compound 2 [μM] |
| 5-FU | — | 30 | — |
| — | Carbatone | — | 1315 |

TABLE 1-continued

| Combination of compounds | | IC$_{50}$ | |
|---|---|---|---|
| Compound 1 | Compound 2 | Compound 1 [μM] | Compound 2 [μM] |
| — | disodium salt of 4-ethyl-2,6-dimethyl-1,4-dihydropyridine-3,5-bis-carbonyloxyacetic acid | — | >2104 |
| — | disodium salt of 2,4,6-trimethyl-1,4-dihydropyridine-3,5-bis-carbonyloxyacetic acid | — | >2694 |
| 5-FU | Carbatone | 6.7 | 0.67 |
| 5-FU | disodium salt of 4-ethyl-2,6-dimethyl-1,4-dihydropyridine-3,5-bis-carbonyloxyacetic acid | 3.7 | 0.37 |
| 5-FU | disodium salt of 2,4,6-trimethyl-1,4-dihydropyridine-3,5-bis-carbonyloxyacetic acid | 1.4 | 0.14 |

IC$_{50}$ for 5-Fluorouracil, disodium salt of carboxylate-methyl ester of 2,6-dimethyl-1,4-dihydropyridine-3,5-dicarboxylic acid (Carbatone) and 2,6-dimethyl-1,4-dihydropyridine-3,5-dicarboxylic acid ester type compounds, with general formula I and combination thereof (in molar ratio 10:1) on viability of human breast carcinoma cells MDA-MB-435s in vitro Comparative experimental results were obtained by using disodium salt of carboxylate-methyl ester of 2,6-dimethyl-1,4-dihydropyridine-3,5-dicarboxylic acid (Carbatone) alone and combine treatment with 5-Fu. Carbatone synergistically potentiates the cytotoxic effect of 5-FU in MDA-MB-435s—Human breast cancer cells, but not so effective as disodium salt of 2,4,6-trimethyl-1,4-dihydropyridine-3,5-bis-carbonyloxyacetic acid and disodium salt of 4-ethyl-2,6-dimethyl-1,4-dihydropyridine-3,5-bis-carbonyloxyacetic acid as it is showed in Table 1.

A possible pharmaceutical composition for oral use exemplifying but not exhausting the present invention is the following formulation of tablet production:

TABLE 2

| Compound of formula I | 1 mg |
|---|---|
| 5-Fluorouracil | 10 mg |
| starch | 20 mg |
| talc | 10 mg |
| Ca stearate | 1 mg |

A possible pharmaceutical composition for oral use exemplifying but not exhausting the present invention is the following formulation of capsule manufacture:

TABLE 3

| Compound of formula I | 1 mg |
|---|---|
| 5-Fluorouracil | 10 mg |
| aerosil | 5 mg |
| lactose | 66 mg |
| talc | 7 mg |
| Ca stearate | 3 mg |

A possible pharmaceutical composition for oral use exemplifying but not exhausting the present invention is the following formulation of solution or/and syrup manufacture:

TABLE 4

| Compound of formula I | 1 | mg/mL |
|---|---|---|
| 5-Fluorouracil | 10 | mg/mL |
| Methyl-p-hydroxybenzoate | 0.20-0.60 | g |
| Propyl-p-hydroxybenzoate | 0.01-0.1 | g |
| Propylene glycol | 6.15-8.30 | g |
| Sorbit | 120.00-150.50 | g |
| Glycerine | 10.00-15.00 | g |
| Purified water | 150 | ml |

The invention claimed is:

1. A 2,6-Dimethyl-1,4-dihydropyridine-3,5-dicarboxylic acid ester type compound selected from those of formula I

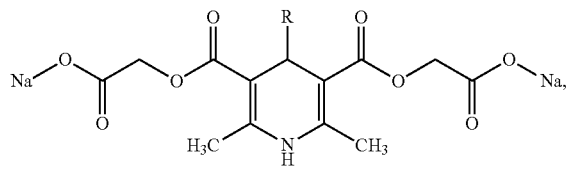

wherein R is a lower alkyl group.

2. The compound of claim 1, wherein R is methyl or ethyl.

3. The compound of claim 1, which is disodium salt of 2,4,6-trimethyl-1,4-dihydropyridine-3,5-bis-carbonyloxyacetic acid, having formula IV

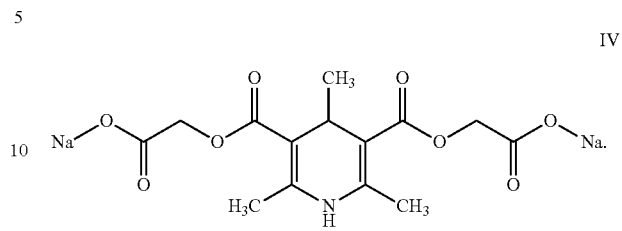

4. The compound of claim 1, which is disodium salt of 4-ethyl-2,6-dimethyl-1,4-dihydropyridine-3,5-bis-carbonyloxyacetic acid, having formula VI

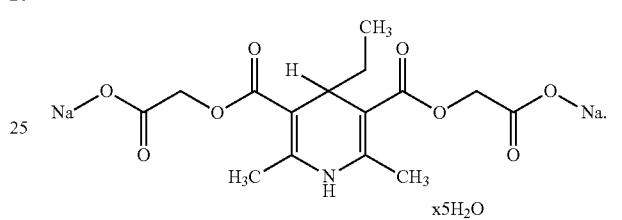

x5H$_2$O

5. A composition comprising a compound of claim 1 in combination with 5-fluorouracil.

6. The composition of claim 5, wherein the ratio of the compound of claim 1 and 5-fluorouracil is from 1:100 to 100:1.

7. The composition of claim 6, wherein the ratio of the compound of claim 1 and 5-fluorouracil is from 1:20 to 20:1.

8. The composition of claim 6, wherein the ratio of the compound of claim 1 and 5-fluorouracil is 10:1.

9. The composition of claim 5, further comprising a pharmaceutically acceptable diluent or carrier.

10. A method of treating breast cancer in a subject in need thereof, comprising administration of an effective amount of a compound of claim 1.

11. A method of treating breast cancer in a subject in need thereof, comprising administration of an effective amount of a composition of claim 5.

* * * * *